US010875744B1

(12) United States Patent
Doyle

(10) Patent No.: US 10,875,744 B1
(45) Date of Patent: Dec. 29, 2020

(54) PASSENGER ELEVATOR AIR PURIFICATION SYSTEM

(71) Applicant: Robert E. Doyle, Houston, TX (US)

(72) Inventor: Robert E. Doyle, Houston, TX (US)

(*) Notice: Subject to any disclaimer, the term of this patent is extended or adjusted under 35 U.S.C. 154(b) by 0 days.

(21) Appl. No.: 16/927,719

(22) Filed: Jul. 13, 2020

(51) Int. Cl.
  *B01D 46/46* (2006.01)
  *B66B 11/02* (2006.01)
  *B01D 46/44* (2006.01)
  *B01D 46/00* (2006.01)
  *B01D 46/42* (2006.01)
  *A61L 9/20* (2006.01)

(52) U.S. Cl.
  CPC ............. *B66B 11/024* (2013.01); *A61L 9/20* (2013.01); *B01D 46/0028* (2013.01); *B01D 46/0043* (2013.01); *B01D 46/4263* (2013.01); *B01D 46/4272* (2013.01); *B01D 46/444* (2013.01); *B01D 46/446* (2013.01); *B01D 46/448* (2013.01); *B01D 46/46* (2013.01); *A61L 2209/12* (2013.01); *A61L 2209/14* (2013.01); *A61L 2209/16* (2013.01); *B01D 2273/26* (2013.01); *B01D 2273/30* (2013.01); *B01D 2279/40* (2013.01)

(58) Field of Classification Search
  CPC ............. B01D 46/448; B01D 46/4263; B01D 46/4272; B01D 46/46; B01D 46/446; B01D 46/444; B01D 46/0028; B01D 46/0043; B01D 2273/30; B01D 2279/40; A61L 2209/16

USPC .............. 55/385.1, 385.2; 454/187, 68, 254; 187/277; 312/236
  See application file for complete search history.

(56) References Cited

U.S. PATENT DOCUMENTS

| 5,718,627 | A | * | 2/1998 | Wicks .................. F24F 11/0001 454/68 |
| 7,059,958 | B2 | | 6/2006 | Santos |
| 7,284,640 | B2 | | 10/2007 | Lee |
| 7,833,310 | B2 | | 11/2010 | Kwon et al. |
| 1,052,730 | A1 | | 1/2020 | Zhao |
| 1,055,677 | A1 | | 2/2020 | Zhao |

(Continued)

FOREIGN PATENT DOCUMENTS

| CN | 2720316 Y | 8/2005 |
| CN | 106066078 A | 11/2016 |

(Continued)

*Primary Examiner* — Minh Chau T Pham
(74) *Attorney, Agent, or Firm* — Sprinkle IP Law Group

(57) ABSTRACT

An air supply system in building elevators for the purpose of providing continuous purified and filtered exterior air for the improved safety of elevator cab passengers. The air supply system is separate from that of the building. System components include: an air intake means in the top of the building to receive exterior air; an air filtering and purifying mechanism; an air blower and compressor; air heating and cooling unit; a pressure controlled air plenum; a flexible vertical lightweight traveling tube that continuously carries purified air from the plenum near the top of the building to the cab interior, a flexible vertical lightweight air exhaust traveling tube that continuously carries spent air from the cab interior discharge conduit to the building exterior exhaust, wherein both tubes are affixed to the elevator traveling cable and extend the height of the building.

20 Claims, 7 Drawing Sheets

(56) References Cited

U.S. PATENT DOCUMENTS

| | | | |
|---|---|---|---|
| 2005/0000754 A1* | 1/2005 | Lee | B66B 11/024 |
| | | | 187/277 |
| 2009/0038473 A1 | 2/2009 | Kwon | |
| 2010/0178862 A1* | 7/2010 | Sahm | F24F 7/06 |
| | | | 454/254 |
| 2015/0216298 A1* | 8/2015 | DeLorean | F24F 13/20 |
| | | | 312/236 |
| 2018/0155921 A1* | 6/2018 | Evert | E04B 1/34321 |
| 2018/0283727 A1* | 10/2018 | Grabon | F24F 7/08 |
| 2019/0299154 A1* | 10/2019 | Meirav | B01D 53/30 |

FOREIGN PATENT DOCUMENTS

| | | |
|---|---|---|
| CN | 207209696 U | 4/2018 |
| KR | 20080047397 A | 5/2008 |
| WO | WO 2006/114856 A1 | 11/2006 |

\* cited by examiner

US 10,875,744 B1

PASSENGER ELEVATOR AIR PURIFICATION SYSTEM

TECHNICAL FIELD

The present invention relates in general to systems for the replacement of air contained in confined spaces such as elevators by means of the continuous exchange of new purified exterior air for the improved safety of elevator cab passengers, which is of critical importance in preventing the spread of air borne viruses. More specifically, the present disclosure relates to the continuous filtering and purifying of ambient air to remove all organic and inorganic airborne impurities which may be found in elevator air systems that could be harmful to passengers. The new purified air continuously replaces old air by exhausting the air stream to the exterior of the confined space so that any potential harm may be removed from the confined space or from the passengers themselves. Air leaks from the elevator hoistway to the cab are suppressed by maintaining the cab air pressure above ambient pressure.

BACKGROUND

In the United States and in other wealthier countries, a large segment of the people work and live in buildings where nearly all of the vertical transportation is done by means of elevators. More often than not, most of their elevator travel while at work is done in the week day rush hours of morning, noon and evening. Then, additional elevator travel is necessary prior to and after working hours for meals, living accommodations and other necessities. Travel by elevator thus very likely subjects a large segment of the population to their closest proximity to other people and therefore the greatest risk of contact with airborne undesirable foreign biological matter, such as bacteria and viruses. People are therefore continually in very confined spaces during a significant part of the day where they are frequently required to suffer the risk of breathing dangerous aerosol contaminants that originate from exterior sources or are expelled by their fellow passengers. In crowded conditions, social distancing is not always an option.

Some of the more frequent and very dangerous contaminants include the deadly corona virus (COVID-19), influenza virus and the common viral head cold, which annually causes significant illness, bed time and lost work time. Death is a risk for many of the more unfortunate. Cases involving the more severe transfer of dangerous air borne viruses include the 1918-1920 Spanish Influenza pandemic where it is estimated that, worldwide, over 500 million were infected, resulting in more than 50 million deaths. Another case is the current ongoing corona virus pandemic where the incredibly high death toll continues to increase each day. These maladies cost an incredible loss of life in addition to the failure of many large and small businesses. Health experts generally agree that the spread of viral pandemics are caused primarily by the very close proximity of people in more cramped public areas such as elevators, busses, trains, subways and taxis which are a vital and very necessary part of everyday living.

That elevators are very important and are used extensively is clear from information published by The National Elevator Industry, Inc., a premier trade association, where they noted that there are about 900,000 elevator units operating in the United States, or about one elevator per 173 working people. A number of units generally serve a single building. Many units have only blower systems in the cab that operate based on a closed loop arrangement where air is taken in from hallways, lobbies and the elevator hoistway and is re-circulated in the cab without purification or even the addition of fresh air. Others have individual air conditioning units generally mounted on the cab exterior that re-circulates the same air in the cab, adding significantly to the weight and operating cost of the elevator. Still other air conditioning systems use hoistway air that is filtered and in some cases purified on the elevator roof, again resulting in added weight and operating costs. The area of the ignored, open and usually dirty elevator hoistway or shaft is rarely seen by passengers, which is likely why so little thought has been given to breathable elevator air until now, under pandemic conditions that may reoccur in the future.

Elevator units currently in operation in the US generally do not provide a means to efficiently supply passengers with direct, continuous purified outside air. Few of the elevators provide an air purification and filtering system that is separate from the building air conditioning system. Virtually all the US elevators are ventilated by air either from the lobby or building floors when the door is opened and from the building elevator hoistway when traveling between floors. The New York City Building Code of 2014 under Section 3004.5.1 requires that one third of the opening that ventilates the elevator hoistway must remain permanently open to outside air to exhaust smoke in the event of a fire, where the hoistway then serves as a smoke chimney. Normally air continues to move upward vertically in the hoistway carrying exhaust from the lobby and all the remaining areas of the building to the exterior top of the building. Other cities have codes similar to those of New York. This requirement makes the treating of elevator shaft air for use in the cab inefficient at best, and more than likely ineffective, since hoistway exhaust air would constantly dilute the already treated air pursuant to rules such as the NYC Building Code.

The embodiments of the invention disclosed herein are based on an air purification and filtering system that operates independently from the building air conditioning system. The equipment required to purify and filter outside air (i.e., air from outside the building) is mounted in the machine room located at the top of the elevator hoistway, and not in or on the cab where the additional weight would substantially increase operating costs. Purified and filtered air is introduced directly into the cabin and exhaust air is removed from the cabin by separate, lightweight traveling tubes attached to the existing elevator travel cable over the height of the elevator shaft.

Supplying cramped public quarters such as elevator cabs with purified and filtered continuous air as disclosed herein provides an effective means of helping to eliminate air borne virus, bacteria and other pathogens. These embodiments will therefore ultimately save lives.

A number of patents involving air treatment have been issued in the past but none have provided for the transfer of purified outside air directly to the interior of the cab. The following U.S. and foreign listings are examples of previous air treatment systems.

U.S. Pat. No. 5,718,627 granted to Edward A. Wicks and published on Feb. 17, 1998 describes a system and procedure for maintaining elevator use during a fire, that includes a blower and a damper at opposite ends of a vertical elevator shaft to create a full volume current of fresh air that engulfs a conventional elevator car traveling between floors. The unidirectional airflow causes a curtain of air that "washes" any smoke away from the exterior of the elevator car and out the exterior exhaust system. When the car stops at a floor, the damper closes to force the fresh airflow onto that location.

Fresh air is chosen from one of several fresh air supplies by sensing the quality of the air at the supply location. This patent is limited to temporary fire emergency incidents and does not provide for an emergency air diverter valve, traveling purified and exhaust air tubes, ultraviolet air purification facilities, continuous air flow and the flow of purified air from the facilities directly into the elevator car, all of which are included in embodiments disclosed herein.

U.S. Pat. No. 7,059,958 issued to Agnaldo Santos and published on Jun. 13, 2006 discloses an elevator cabin with an integrated ventilation system. A fan is attached to the elevator cabin and a vertical side wall of the elevator cabin has a plurality of distributed ventilation holes. At least one air channel element is attached to the side wall, so that the air channel element together with the adjacent portion of the side wall forms an air channel. An adapter element is situated between the fan and an inlet opening of the air channel for guiding air from the fan into the air channel so that the air travels from the fan through the adapter element into the air channel and through the ventilation holes into the elevator cabin. This patent is limited to the circulation of existing cabin air only and does not provide for traveling purified and exhaust air tubes, ultraviolet air purification facilities, emergency air diverter, continuous air flow and the flow of purified air from the facilities directly into the elevator cabin, all of which are included in embodiments disclosed herein.

U.S. Pat. No. 7,284,640 granted to Nien-Chin Lee and published on Oct. 23, 2007 proposes a system to enhance air quality that could include a multi level building having a hoistway vertically extending through at least two levels of the building, for receiving a car vertically moving therein. The system could further include at least an air circulating device placed on a top level of the building for pumping exterior air into the hoistway, a plurality of current directing devices installed between different levels of the building for directing air in the hoistway flowing from an upper level of the building to a lower level of the building, and a waste discharge device in communication with an available exhaust outlet in a basement for discharging exhaust out of the hoistway. Accordingly, the air lowing in the hoistway is maintained in a single direction. With the system of enhancing air quality for buildings, dirty air discharged below the car is maintained to flow downwardly to prevent backflow of the dirty air, so as to achieve better air quality in the elevator. This patent is limited to the unidirectional flow of untreated hoistway air only and does not provide for traveling purified air and air exhaust air tubes, ultraviolet, air purification facilities, emergency air diverter, continuous air flow and the flow of purified air from the air processing facilities directly into the elevator cabin, all of which are included in embodiments disclosed herein.

U.S. Pat. No. 7,833,310 issued to Jun Hyoun Kwon, Rae Eun Park and Eun Ju Ha on Feb. 12, 2009 discloses an elevator including a cage which moves in a vertical direction of a building and an air filter which purifies the air inside the elevator cage. The air filter includes an ion generator which generates ions by a plasma discharge to move the ions into the cage, a dust sensor which detects a dust contamination level in the cage, and a controller which compares the dust contamination level detected by the dust sensor with a predetermined standard contamination level and operates the ion generator. However, a 2013 comprehensive British review of 80 years of research into air ions and respiratory function outcomes found that there was no clear support for any beneficial role in respiratory function, nor evidence for significant detrimental effect using ion generators. Instead, filtering and treating air with ultraviolet systems has long been the preferable means of removing viruses, bacteria and other undesirable organic material and dust. This patent is limited to re-cycling and removing dust solids from hoistway air only and does not provide for traveling purified and exhaust air tubes, ultraviolet air purification facilities, emergency air diverter, continuous air flow and the flow of purified air from the facilities directly into the elevator cabin, all of which are included in embodiments disclosed herein.

U.S. Pat. No. 10,527,309 issued to Jianwei Zhao, Qiang Li, Lijia Zhao, Sanming Wen and Jiahuan Zhou on Jan. 7, 2020. A building air conditioning control system for controlling the temperature includes: a first head counting module to acquire first head count change data of a floor area according to a weight change of a cabin of an elevator when passing the corresponding floor area; a second head counting module to acquire second head count data change of the floor area according to data acquired by an image sensor mounted in the corresponding floor area; and an air conditioning control module to correct head count change data based on the first head count change data and the second head count change data and control the comfort degree of air in the floor area based on the corrected head count change data. Air conditioning of the cabin is thus reduced or increased based on the head count data in an effort to conserve power and reduce costs. This patent is limited to the control of cabin and elevator hoistway air only and does not provide for traveling purified and exhaust air tubes, ultraviolet air purification facilities, continuous air flow, emergency air diverter, and the flow of purified air from the facilities directly into the elevator cabin, all of which are included in embodiments disclosed herein.

U.S. Pat. No. 10,556,776 issued to Chen qian Zhao and Kyle B. Martin on Feb. 11, 2020. An illustrative example elevator traveling cable includes a plurality of conductors configured for conducting at least one of electrical energy and communication signals. A jacket covers the plurality of conductors. At least one load bearing member supports a weight of the traveling cable and comprises liquid crystal polymer which is lighter in weight than conventional metal cable, thus reducing power costs. This patent concerns only the selection of liquid crystal polymer as the composition of the traveling cable of choice and does not provide for traveling purified and exhaust air tubes, ultraviolet air purification facilities, emergency air diverter, continuous air flow and the flow of purified air from the facilities directly into the elevator cabin, all of which are included in embodiments disclosed herein.

Chinese Pat. No. 2720316Y received by Pan Xiaoming and published on Aug. 24, 2005 relates to a fresh air purifying system for an elevator cab, which comprises an elevator hoistway and an elevator cabin positioned in the elevator hoistway. The top of the elevator hoistway contains an air blower passage that connects the hoistway to exterior fresh air. The bottom of the elevator hoistway is provided with an air exhaust passage connected to an air exhaust fan. The top of the elevator cab is provided with a fresh air purifier in which an air mixing means is located. The bottom of the air mixing means communicates with the elevator cab via a diffusing air port, and the top of the air mixing means communicates with the elevator hoistway via a fan. The system processes the air for the elevator cabin via sections of ventilation, air sterilization and air purification. This patent concerns the treatment of fresh air for transfer to the open elevator hoistway that is then vented into the cabin following treatment. This patent calls for air ventilation, purification and purification equipment to be mounted on the cabin roof which adds significant weight that substantially increases power costs. The current invention teaches that, because of the significant weight addition, all air processing equipment be mounted in the machine room at the top of the building to service traveling light weight purified and exhaust air tubes that protect from hoistway air, offer controlled air flow and the flow of purified air from the ultraviolet air processing facilities directly into the elevator cabin. This patent does not include an emergency air diverter to protect passengers from breathing smoke.

Chinese Pat. No. 106066078A assigned to Shanghai Step Electric Corp. and published on Nov. 2, 2016 discloses an elevator cabin console monitor that contains the means to monitor and control air quality through a link to an air mass sensor and air cleaner mounted in the cabin, adding significantly to the weight and operating costs. The air mass sensor determines the quality of the air within the car through reading of the concentration of parts per million solid content suspended in the air. The air quality automatically meets the preset default conditions as provided in the control mainboard by adjusting the air quality through ultraviolet means applied to the cabin interior where the cabin air is also pre-filtered. The vertically traveling elevator cabin receives the air supply and exhausts spent air by means of air ducts with fans to move air in and out of the elevator shaft in which it travels. This patent teaches only the monitoring and operation of the air mass sensor and does not provide for traveling purified and exhaust air tubes, ultraviolet air purification facilities, emergency air diverter, continuous air flow and the flow of purified air from the facilities directly into the elevator cabin all of which are included in embodiments disclosed herein.

Chinese Patent No. CN207209696U granted to Suzhou Tianyurun Elevator Parts Co. Ltd. on Apr. 10, 2018 discloses a system for enhancing air quality for buildings, where the system includes a multi level building having a hoistway vertically extending through at least two levels of the building for travel of a vertically moving elevator cab. Elevator interior air purification processing equipment consisting of illuminating lamp installed in the left of the inner upper end of the car. A gas pressure detector is installed on the right side of the inner upper end of the car. A humidifier is mounted in the right hand external area of the car, an air pressure fan is provided with the right side of the humidifier, with an installed air storage chamber, the outer upper ends of the air storage chamber being provided with an air pump, and the upper end of the air pump being provided on the right side of the pressure fan. A first active carbon layer is provided, the upper end of first active carbon layer having a first partition, and the upper end of the first partition is having one screen pack, where the upper end of first screen pack is provided with a second partition. The upper end of the second partition is provided with a breather pipe and a gettering container is installed on the right of the outer upper ends of shell, with the upper end of the gettering container being provided with air cleaning box. The upper end for changing case is provided with a fixed mount, and an outlet box is provided outside the lower end of the shell. This patent calls for heavy air purification equipment to be located in the cab which will result in excessive operating lift costs in contrast to this invention which has the equipment located in the machine room at the top of the elevator hoistway with light weight purified air and exhaust air traveling tubes extending from the machine room to the passenger cabin for direct supply. This patent also does not include either emergency diverter or ultraviolet air purification means whereas embodiments disclosed herein do call for such facilities.

PCT Patent App. No. WO2006114856A1 by Hayashi Yuichiro, et al. was published on Nov. 2, 2006. Since the cooling unit for the hoistway equipment is large and consumes a large amount of power, the installation cost and the operating cost are high. Therefore, an elevator hoistway heat diffusing device is considered which is a simple mechanism that consumes less power and has low installation and operating costs. In a machine room-less type elevator in which the driving device and a control device are arranged in the upper part of the hoistway, a blower is mounted in the upper part in the hoistway with one end in the vicinity of the control device or the driving device. An intake duct has an intake port and the other end attached to the intake side of the blower, with one end attached to the exhaust side of the blower and the other exhaust port being arranged to exhaust air below the hoistway in an elevator hoistway heat diffusion device including an exhaust duct. This patent is limited to the cooling of elevator hoistway equipment only and does not provide for traveling purified and exhaust air tubes, ultraviolet air purification facilities, emergency air diverter, continuous air flow and the flow of purified air from the facilities directly into the elevator cabin all of which are included in embodiments disclosed herein.

Korean Pat. No. KR20080047397A of Mitsubishi Electric Corp. was published on May 28, 2008. This patent application concerns the design of an elevator mechanism that can efficiently suppress the operating temperature rise of the top of the hoistway due to the elevator drive equipment. The elevator apparatus according to the present invention includes a drive device installed in the top of the elevator hoistway, a cab for raising and lowering within the hoistway by the drive device and an upper air supply and exhaust mechanism located above the entrance of the top floor in the hoistway with an exhaust duct having a lower air supply and exhaust opening located below the upper air supply and discharge in the hoistway. The hoistway contains a vertical partition extending the length of the hoistway that, by means of ventilation ducts, serves as a conduit for the vertical movement of hoistway air that is the result of the vertical travel of the cab. The air on one side of the partition moves one direction while the air on the opposite side of the partion moves in the opposite direction, thus forming a circular ventilation cell around the partition. In effect, the vertical cab movement serves as an air piston. It is this circular movement of air that provides ventilation to suppress the operating temperature at the top of the hoistway. This patent is limited to the cooling of elevator hoistway equipment only and does not provide for traveling purified and exhaust air tubes, emergency air diverter, ultraviolet air purification facilities, continuous air flow and the flow of purified air from the facilities directly into the elevator cabin all of which are included in embodiments disclosed herein.

U.S. Pat. App. No. US2009038473A1 of Kwon et al., published on Feb. 12, 2009 discloses a system for improving air quality for vertical travel in buildings, where the system includes an elevator having an air cleaning apparatus, and an air cleaning control means to filter and purify air inside the elevator by removing various harmful substances including air borne fine dust, virus, bacteria and other similar pathogens. The air cleaning apparatus includes a filter, an ion generator, a dust sensor, and a control panel. The filter eliminates dust in the air, the ion generator generates ions by plasma discharge to remove fine dust passing through the filter, the dust sensor detects the pollution level of the air, and the control panel operates the ion generator with a predetermined pollution level tolerance for pathogen removal. However, a 2013 comprehensive British review of 80 years of research into air ions and respiratory function outcomes found that there was no clear support for any beneficial role in respiratory function, nor evidence for significant detrimental effect using ion generators. The time tested and accepted means of purifying air today consists of ultraviolet air treatment which is included with this invention. The source of all new supply air is extracted from the elevator hoistway thus the patent does not provide for traveling purified and exhaust air tubes, emergency air diverter, continuous air flow and the flow of purified air from the facilities directly into the elevator cabin all of which are included in embodiments disclosed herein.

SUMMARY

The present disclosure details systems and methods for providing continuous purified and filtered exterior air for the improved safety of elevator cab passengers. Exemplary embodiments are separate from that of the building, and components of the system may include: an air intake means in the top of the building to receive exterior air; an air filtering and purifying mechanism; an air blower and compressor; air heating and cooling unit; a pressure controlled air plenum; a flexible vertical lightweight traveling tube that continuously carries purified air from the plenum near the top of the building to the cab interior, a flexible vertical lightweight air exhaust traveling tube that continuously carries spent air from the cab interior discharge conduit to the building exterior exhaust, wherein both tubes are affixed to the elevator traveling cable and extend the height of the building.

One embodiment comprises a system for processing air for a passenger elevator using traveling conduits. The system has an exterior air inlet positioned to receive exterior air (e.g., at or near the top of the building in which the elevator is installed) and a first air conduit which has a first end coupled to the exterior air inlet and a second end configured to be coupled to an elevator cab, where the first air conduit is configured to deliver the exterior air to the elevator cab. The system includes an air handler which is coupled to the first air conduit and is configured to pressurize the exterior air and cause the exterior air to flow into the elevator cab. The system further includes a second air conduit having a first end configured to be coupled to the elevator cab and a second end configured to be coupled to an exhaust exit port, where the second air conduit is configured to exhaust air from the elevator cab to the exhaust exit port. In this embodiment, the first air conduit and the second air conduit are both traveling conduits that are configured to maintain their respective couplings to the elevator cab. The first air conduit can therefore continue to deliver the exterior air to the elevator cab and the second air conduit can continue to exhaust air from the elevator cab to the exhaust exit port while the elevator cab travels through a hoistway of a building.

In this embodiment, the first air conduit is separate from a building heating, ventilation and cooling (HVAC) system. The first air conduit comprises an exterior air conduit located in an uppermost area of the building, the exterior air conduit being coupled between the exterior air inlet and the air handler, the first air conduit further comprising a processed air conduit that is coupled between the air handler and the elevator cab. In one embodiment, the air handler includes an air filter, and an air purifier, and at least one of a heater and a cooler. The air handler is configured to provide pressurized, processed air to a pressure plenum, and the pressurized, processed air in the pressure plenum is delivered to the processed air conduit. The air purifier may comprise one or more ultraviolet air purifier units located in the uppermost area of the building which regulate the purity of ambient supply air as required by the control system to meet pre-set requirements. ("Uppermost" is used herein to refer to locations at or near the top of a building, but these locations need not be the highest point of the building or even the top floor.) The traveling conduits in some embodiments comprise lightweight corrugated plastic conduits. The first and second air conduits may be secured to a pre-existing traveling electrical cable that is connected to the elevator cab to carry power and control signals.

In some embodiments, the system may include one or more emergency valves that are coupled to the first and second air conduits. In these embodiments, the system is configured to operate alternately in either a normal operational mode or an emergency mode. In the normal operational mode, the emergency valves are positioned to enable the flow of exterior air through the first air conduit, the elevator cab and the second air conduit. In the emergency mode, the one or more emergency valves are positioned to block the flow of exterior air into the elevator cab from the first air conduit and to block the exhaust of air from the elevator cab out through the second air conduit. A closed loop may thereby be formed to circulate air through the elevator cab. An emergency air source (e.g., bottled air) may be provided so that, in the emergency mode, the emergency air source is coupled to the first air conduit and provides air to the elevator cab through the first air conduit.

The system may include a control system which is coupled to the air handler and includes one or more sensors and a monitor which are jointly operable to record and control conditions such as the quality, flow rate, temperature and pressure of air being processed by the air handler. The air handler may include an air filter an air purifier, and a system controller which is operable in manual or automatic modes. In the automatic mode, the system controller automatically adjusts the air filter and purifier to predetermined levels, while in the manual mode these levels manual and remote operation of the air filter and purifier is enabled. The control system may be configured to monitor and control: an exterior air conduit located in an uppermost area of the building and thereby regulate a supply rate of exterior air; one or more air filter systems coupled with air blowers that are located in an uppermost area of the building and thereby regulate a supply rate of exterior air; one or more heating, ventilation, air conditioning (HVAC) units and thereby regulate the temperature of the air supplied to the elevator cab; the pressure plenum and thereby regulate the pressure of the air supplied to the elevator cab; an air supply rate in the first air conduit to meet predetermined flow rate requirements; and an air exhaust rate in the second air conduit to meet predetermined flow rate requirements.

Numerous alternative embodiments may also be possible.

These, and other, aspects of the disclosure will be better appreciated and understood when considered in conjunction with the following description and the accompanying drawings. It should be understood, however, that the following description, while indicating various embodiments of the disclosure and numerous specific details thereof, is given by way of illustration and not of limitation. Many substitutions, modifications, additions, or rearrangements may be made within the scope of the disclosure without departing from the spirit thereof, and the disclosure includes all such substitutions, modifications, additions, or rearrangements.

BRIEF DESCRIPTION OF THE DRAWINGS

The drawings accompanying and forming part of this specification are included to depict certain aspects of the disclosure. It should be noted that the features illustrated in the drawings are not necessarily drawn to scale. A more complete understanding of the disclosure and the advantages thereof may be acquired by referring to the following description, taken in conjunction with the accompanying drawings in which like reference numbers indicate like features.

DETAILED DESCRIPTION

Figure 1:
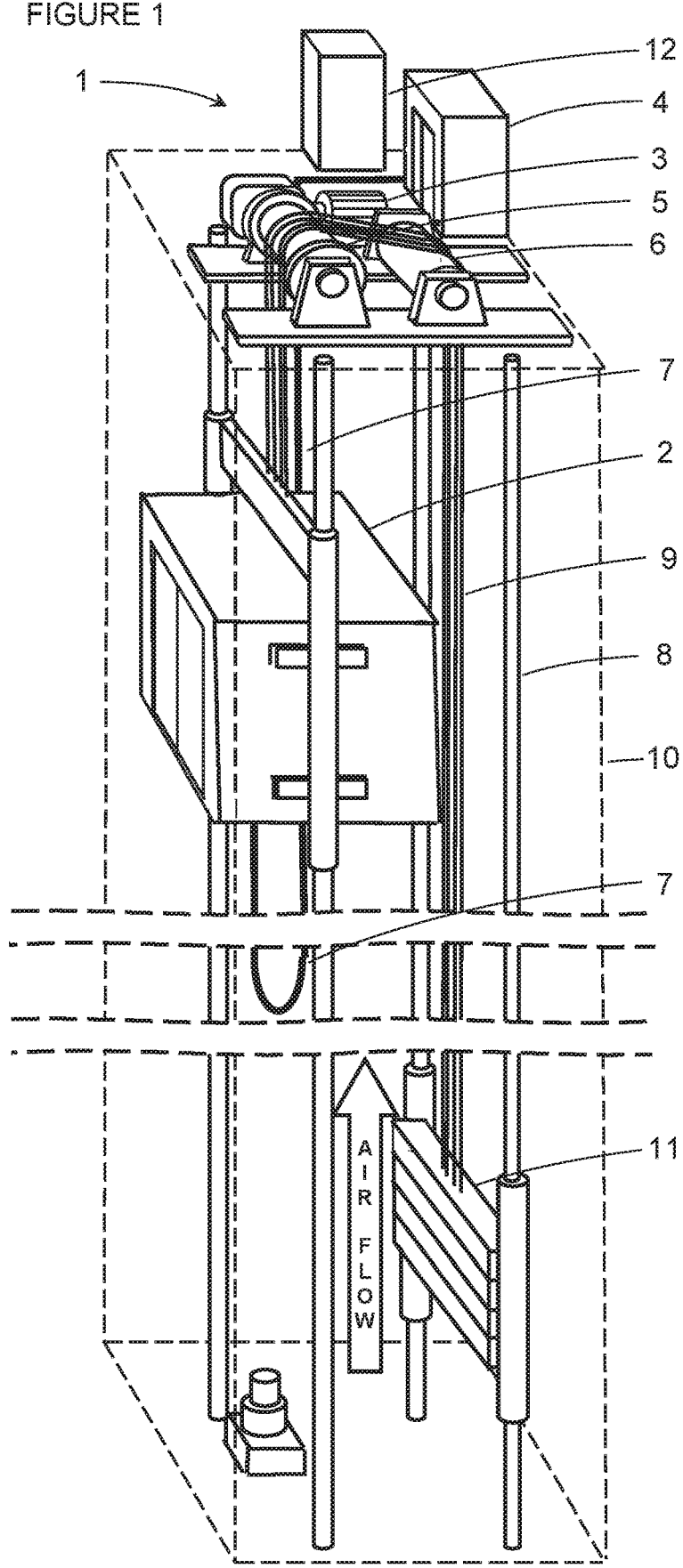
FIG. 1 is a schematic diagram of a passenger elevator showing a cab, lift cables, counter weights, guide rails and sheaves.

Embodiments and the various features and advantageous details thereof are explained more fully with reference to the non-limiting embodiments that are illustrated in the accompanying drawings and detailed in the following description. Descriptions of well-known starting materials, processing techniques, components and equipment are omitted so as not to unnecessarily obscure the embodiments in detail. It should be understood, however, that the detailed description and the specific examples are given by way of illustration only and not by way of limitation. Various substitutions, modifications, additions and/or rearrangements within the spirit and/or scope of the underlying inventive concept will become apparent to those skilled in the art from this disclosure.

Referring to the figures, the principles of the invention are explained by describing in detail specific example embodiments of devices, systems and methods for providing filtered purified air for elevator passengers. Those skilled in the art will note that the invention may be embodied as many other devices, systems, and methods. Many modifications and variations will be apparent to those of ordinary skill in the art. Exemplary embodiments herein are described in order to best explain the principles of the invention and the practical application, and to enable others of ordinary skill in the art to understand the invention for various embodiments with various modifications as are suited to the particular use contemplated. The scope of the invention is not intended to be limited by the details of exemplary embodiments described herein. The scope of the invention should be determined through study of the appended claims.

Aspects of the present invention are described below with reference to drawings and flowchart illustrations of methods according to embodiments of the invention. Specific design details have been provided for illustration, but should not be considered limiting. Readers of skill in the art will recognize that many variations of air filtration and purification systems may be implemented consistent with the scope of the invention as described by the appended claims.

Generally, aspects of the disclosure concern the filtration and purification of air for use in extremely congested spaces, such as passenger elevators in buildings, for the improved safety of the public. In one embodiment, processing of air captured from the exterior of a building is done first by an intake blower coupled with a filtration screen to capture larger particles such as dust or larger organic particles. Much smaller submicroscopic organic particles not captured by filtration such as viruses, bacteria and other similar pathogens are destroyed by passing the filtered air through an ultraviolet or similar chamber. Processed air then passes through heating or cooling facilities following which it is blown into a pressure plenum from which the air is transmitted into a flexible lightweight corrugated tube the length of the elevator traveling cable and is affixed to the cable. The tube is connected to the cabin and delivers the processed air for passenger consumption. Exhaust air is carried to the exterior of the building by means of a flexible lightweight corrugated tube extending from the cabin, the length of the elevator traveling cable and is affixed to said cable. Exhaust air also escapes into the hoistway through areas around the elevator doors that are generally not fully sealed. Air pressure in the cabin is therefore maintained at a level slightly above ambient air pressure to avoid exhaust air from the hoistway passing into the cabin. All air processing equipment is mounted in the machine room at the top of the hoistway, and not on or in the cab, which significantly reduces electric power costs. Sensors and control mechanisms are not shown in most of the diagrams.

FIG. 1 is a schematic drawing of an example elevator system 1 containing an elevator cab 2 with an electric motor 3 and power cabinet 4 providing electricity to the drive sheave 5 and electricity for the traveling cable 7. The deflector sheave 6 creates vertical traveling space for movement between the cab 2 and the counter weight 11 both of which are connected by four cables 9 joining the cab 2 and the counterweights 11 for vertical movement in the hoistway 10. The traveling cable 7 carries electricity, control signals and other appliances for the cab 2. Cable 7 is referred to as a "traveling" cable because it maintains a connection to the elevator cab 2 as it travels up and down hoistway 10, allowing power and control signals to be communicated between cab 2 and stationary components such as electric motor 3 and power cabinet 4. There are four guide rails 8 that maintain correct horizontal alignment of the cab 2 and the counterweight 11. The invention equipment is not shown in FIG. 1.

Figure 2:
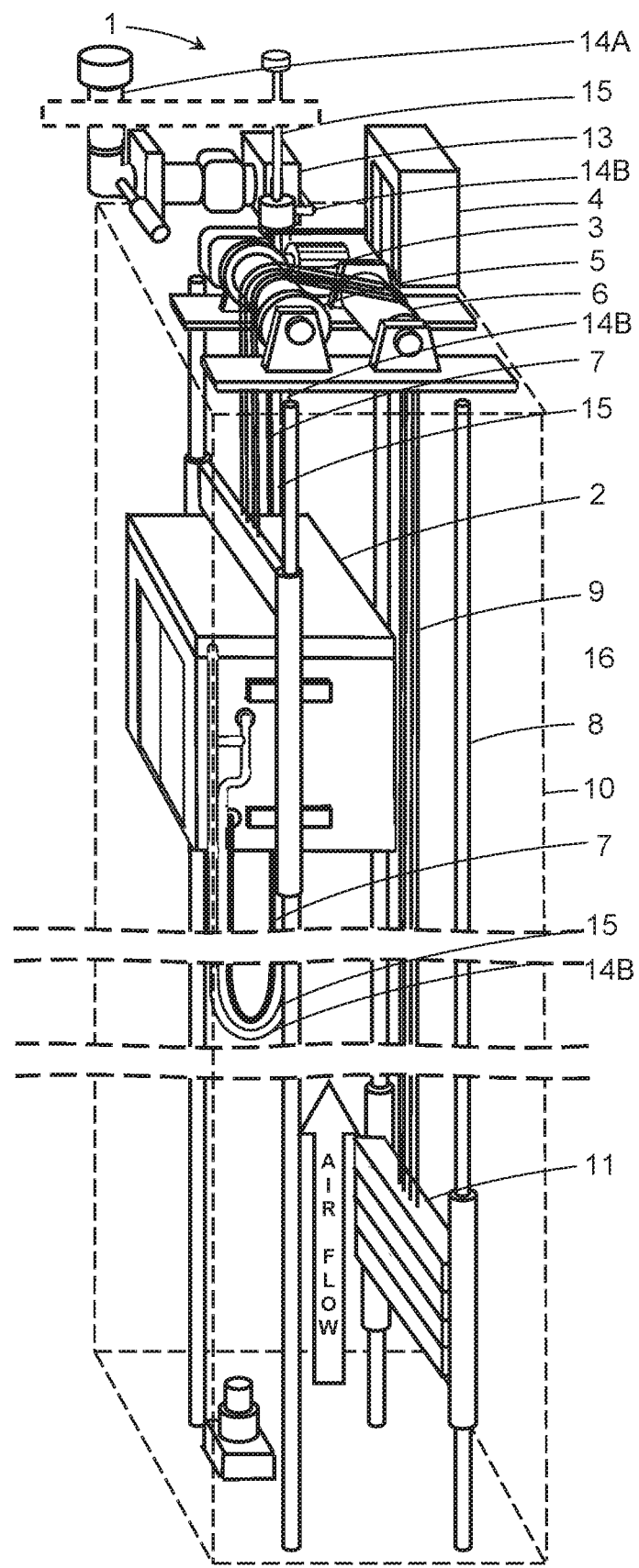
FIG. 2 is a schematic diagram of a passenger elevator showing a cab, lift cables, counter weights, guide rails and sheaves in accordance with some embodiments.

FIG. 2 is essentially identical to FIG. 1, except that the invention equipment is depicted in this illustration in accordance with embodiments of the present disclosure. The invention equipment as described in FIGS. 3, 4, 5, 6 and 7 includes an air handler which in this case incorporates a processing array 13 located in the machine room (not shown) at the top of the elevator system 1. The air handler receives exterior air from exterior air conduit 14A. The exterior air enters an inlet of conduit 14A and is filtered, purified and heated or cooled and pressurized for intermediate storage in the plenum, a component of the air processing array 13. For the purposes of this disclosure, "exterior air" refers to air that is provided from a source that is generally free from undesirable aerosol contaminants and foreign biological matter such as bacteria and viruses, and is not recirculated from the cab 2, hoistway 10 or other sources that present an increased risk of illness. In some embodiments, the inlet of conduit 14A is positioned at or near the top of the building in which the elevator is installed, away from any hoistway or similar exhaust. The inlet of conduit 14A need not be positioned at the top of the building, but may be positioned at any suitable location at which the exterior air is unlikely to contain undesirable contaminants.

The filtered, purified and pressured air then enters processed air conduit 14B, which is a flexible lightweight tube (e.g., a corrugated tube) affixed to the traveling cable 7 and extending from the air processing array 13 to cab 2 for passenger consumption. Cab 2 exhaust air is conveyed from cab 2 to the building exterior through exhaust air conduit 15, which extends from the cab to the exhaust exit port above the top of elevator system 1. In this embodiment, conduit 15 is a flexible lightweight corrugated tube affixed to the traveling cable 7 in the same manner as conduit 14B. The remaining items illustrated in the figure consist of an electric motor 3 and power cabinet 4 providing electricity to the drive sheave 5, the deflector sheave 6 that creates vertical space for movement between the cab 2, and the counter weight 11 both of which are connected by four cables 9 joining the cab 2 and the counterweights 11 for vertical movement. The traveling cable 7 carries electricity, control signals and other appliances for the cab 2. There are four guide rails 8 that maintain correct traveling alignment of the cab 2 and the counterweight 11. The elevator system 1 is housed by the hoistway 10.

Because conduits 14B and 15 maintain connection between cab 2 and the stationary equipment (e.g., exterior air conduit 14A, air handler and processing array 13, and the exhaust exit port), these conduits may be referred to herein as traveling conduits. As explained in more detail below, the traveling conduits allow the stationary components to be located at stationary positions at the top of hoistway 10, rather than being mounted on cab 2 itself. This provides such benefits as reducing the weight of the cab, thereby reducing the energy usage of the system, and also enabling a continuous flow of exterior air (which may be filtered, purified, etc.) directly into the elevator.

Figure 3:
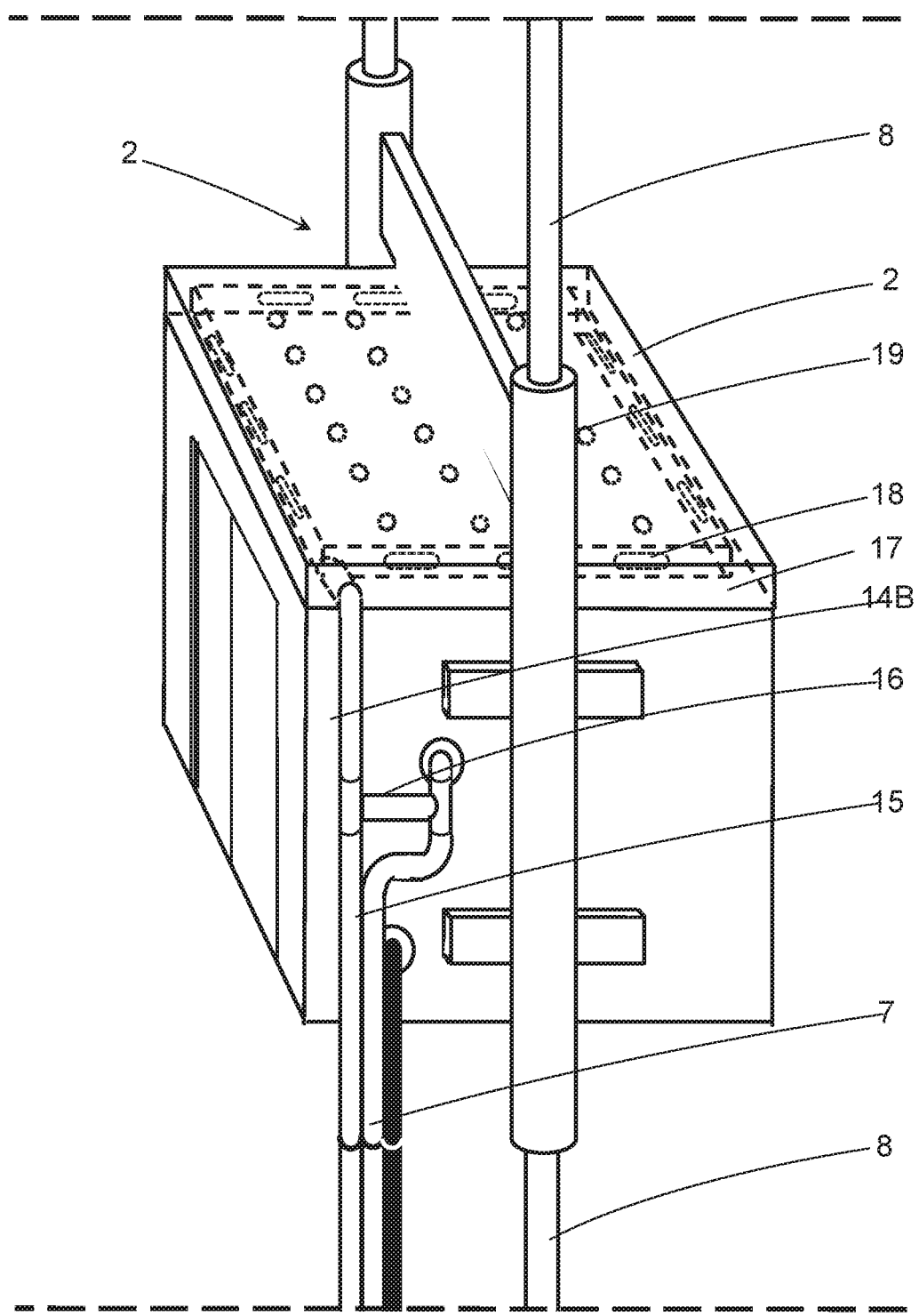
FIG. 3 is s schematic diagram of the passenger elevator cab, guide rails and part of the air circulation system in accordance with some embodiments.
Figure 4:
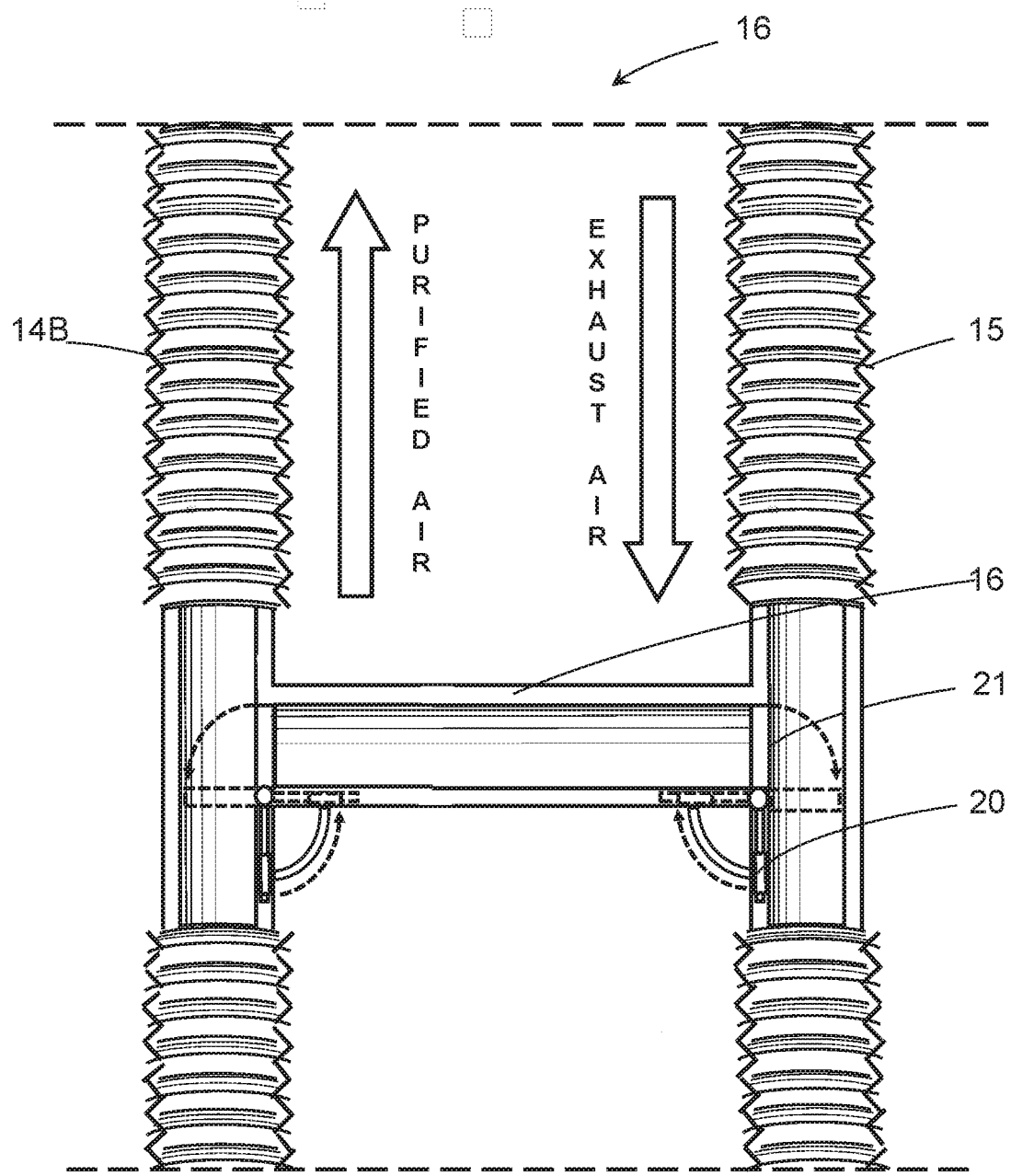
FIG. 4 is a schematic sagittal section diagram of the air emergency valve arrangement in accordance with some embodiments.

FIG. 3 is a schematic drawing of the cab 2, guide rails 8 and processed air circulation pathways in accordance with embodiments of the present disclosure. The travel cable 7 is affixed to processed air conduit 14B and exhaust air 15 in the lower left side area of the cab 2. The air emergency valve mechanism 16 detail is illustrated in FIG. 4 and may be used in the event of a fire or similar emergencies. Filtered and purified air entering the cabin 2 through processed air conduit 14B in the upper air chamber 17 and with the aid of blowers first flows into elongate ports 18 and thence distributively into entry ports 19 at the roof of the cab 2 for passenger consumption. Exhaust air moves into gathering chambers (not shown) from the lower perimeter areas of the cab 2 and is collected for disposal at the building exterior by conduit 15.

FIG. 4 is a schematic drawing of a sagittal section of air emergency valve mechanism 16 illustrating the flow of processed air conduit 14B and exhaust air conduit 15 for normal and emergency conditions. Under normal operating conditions processed air conduit 14B and exhaust air conduit 15 flapper valve 21 is in the vertical position as shown, indicating that input air in processed air conduit 14B and exiting air in exhaust air conduit 15 are flowing as designed.

In the case of a fire or other emergency affecting air quality, in order to avoid smoke or other harmful gasses, the cabin air may be isolated by forming an air flow loop. This is accomplished by automatically rotating both flapper valves 21 some 90 degrees to the horizontal position as shown by the dashed line images. Rotation is performed by flapper valve electric driver 20. This action eliminates both the input of processed air in conduit 14A and the output of exhaust air in conduit 15, where all new outside air and exhaust air flow is stopped. The air then flows in an isolated loop, eliminating the danger of bringing smoke into the cab while still circulating breathable air.

Figure 5:
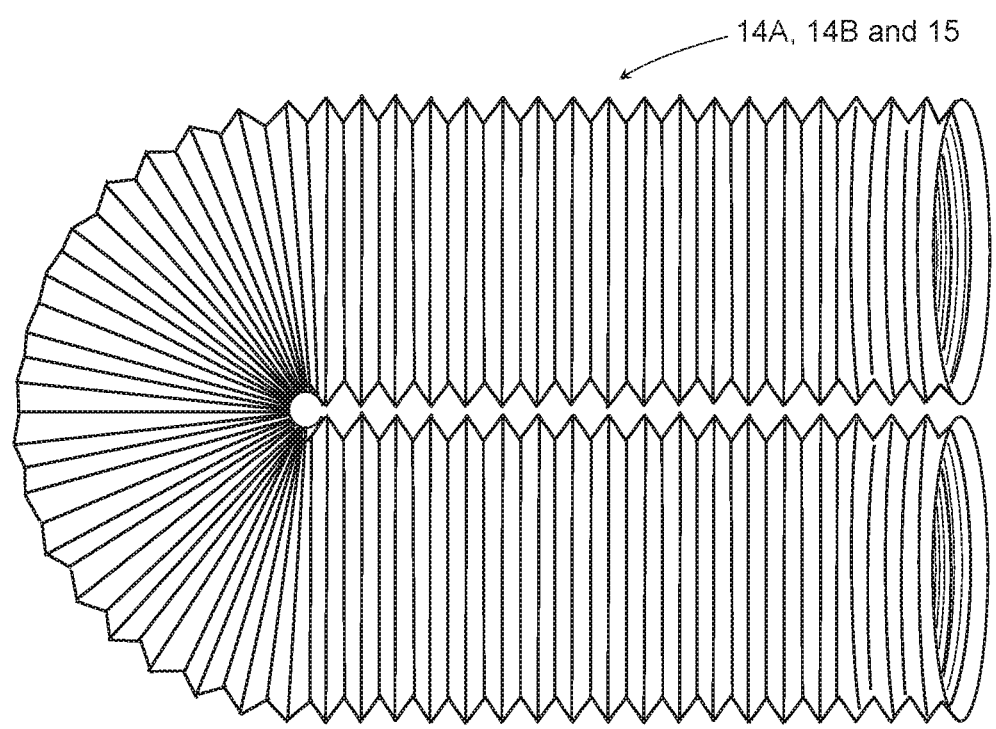
FIG. 5 is a schematic diagram of a segment of an air conduit in accordance with some embodiments.

FIG. 5 is a sketch of a segment of the type of single wall corrugated robust plastic tubing that could be used for exterior air conduit 14A, processed air conduit 14B and exhaust air conduit 15 in accordance with embodiments of the present disclosure. This segment was drawn in the form of a "U" to illustrate its flexibility. The flexibility of the conduit allows it to hang below the cab 2 in the same manner as traveling cable 7. This type of conduit is also very lightweight, with suitable sizes of conduit commonly weighing less than 0.5 pounds per foot, so that it adds relatively little weight to the system. Single wall corrugated tubing is a common item and is manufactured by a number of companies. The conduit may have any suitable diameter (e.g., 3-6 inches inner diameter) and wall thickness (typically about 0.002 inches).

One particular example of a conduit that may be used in embodiments of the invention is a four inch inside diameter polyethylene corrugated tubing with a wall thickness of 0.002 inches, a corrugation width (the distance from the top to the bottom of the corrugation) of 0.35 inches, and weighs 0.325 pounds per foot. Thus, as an example, for a 20 story building, the total weight of a conduit using this type of tubing would only be about 78 pounds (for a 20 story vertical length of approximately 240 feet). When the cab 2 is positioned at the lowest floor of the building, the weight supported by processed air conduit 14B, for example, would be nearly zero at the cab connection, while the weight supported by the stationary uppermost connection of processed air conduit would be 78 pounds. Alternatively, when the cab 2 is positioned at the highest floor of the building the weight supported by processed air conduit 14B would be 39 pounds at the cab 2 connection, with the weight supported by the stationary uppermost connection of processed air conduit 14B also being 39 pounds. The same example applies for exhaust air conduit 15. The air processing array 13, which is the heaviest part of the system, would be placed in the machine room in the top area of the hoistway. By placing the air processing array 13 in the machine room, rather than on the cab 2, power costs would be reduced when compared to prior designs where the air conditioning and other air processing equipment are contained on or in the cab (which results in additional travel weight and higher operating costs). Additionally, having the air processing array 13 in one location in the machine room allows much easier and safer inspection and maintenance of these components, and would not necessarily require shut down of the elevator for the inspection. Thus, having the same equipment on or in the cab for inspection and maintenance would not as safe as the invention and would require shut down of the elevator and lost travel time.

Figure 6:
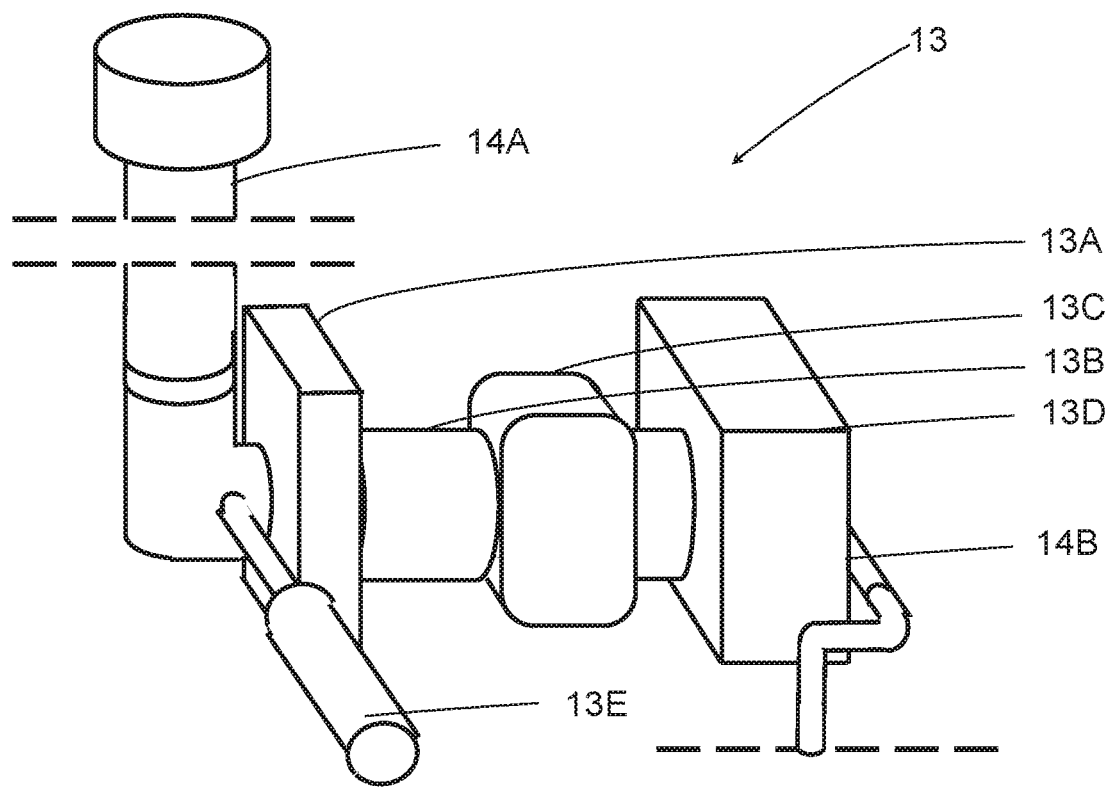
FIG. 6 is a schematic diagram illustrating a filter, purification, air temperature, and pressure system in accordance with some embodiments.

FIG. 6 is a schematic drawing of the air processing array 13 in accordance with embodiments of the present disclosure. Air processing array 13 is located in the machine room (not shown) in the top area of the elevator system 1 and includes: exterior air conduit 14A located in the outside top area of the building which on command receives exterior air that then is passed by blower through air filter 13A to the ultraviolet purifier 13B and may be heated or cooled in HVAC chamber 13C and finally pressurized for intermediate momentary storage in the pressure plenum 13D. On command, processed air then enters conduit 14B, a flexible lightweight corrugated tube extending from the pressure plenum 13D to the cab 2, being affixed to the travel cable 7 (not shown here) and exhaust air conduit 15 (not shown here). Emergency high pressure air bottle 13E is a secondary back up temporary air source used in the event exterior air cannot be used where conduit 14A is shut off, and air bottle 13E is opened while the remainder of processing array 13 continues operation.

Figure 7:
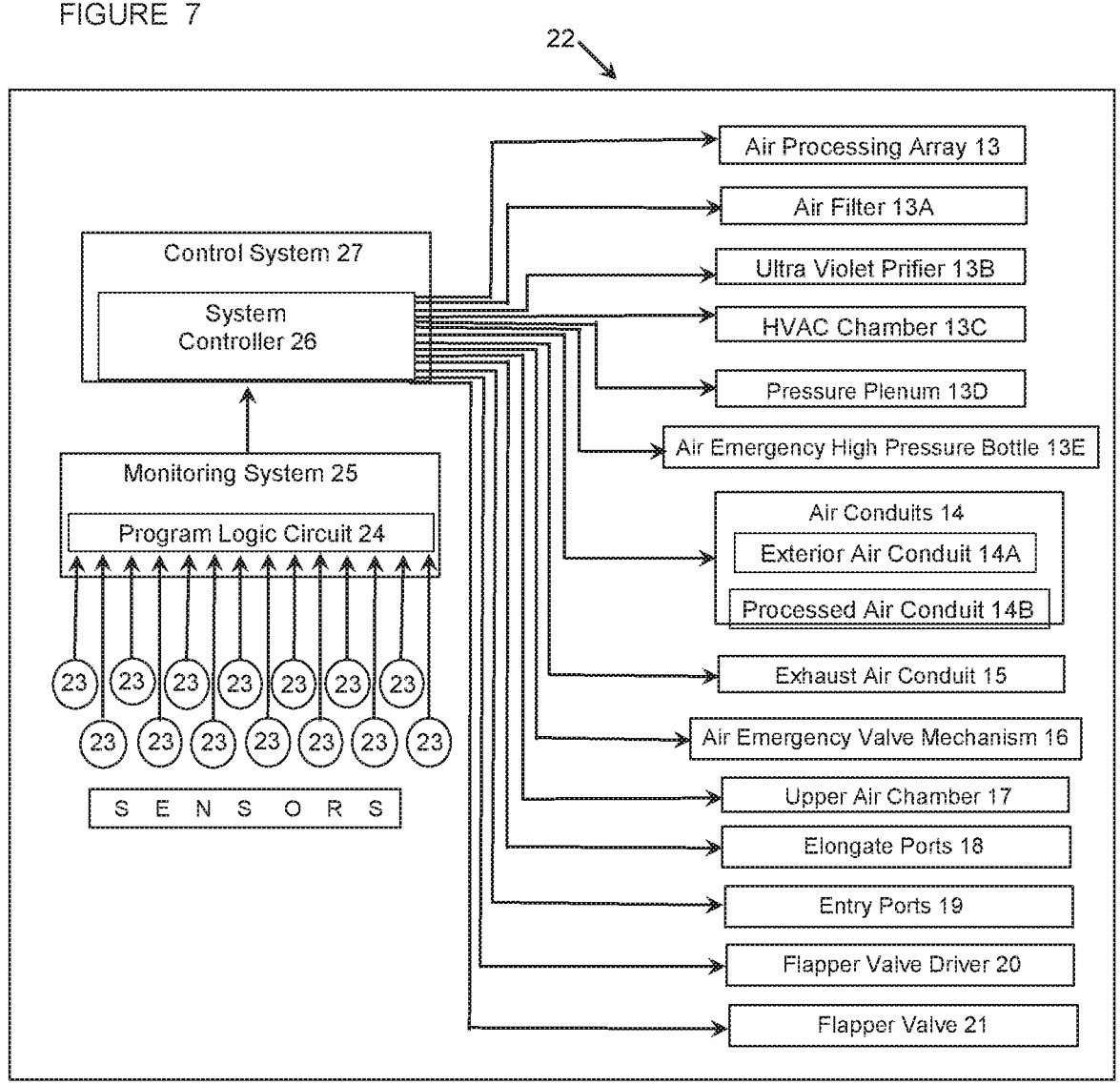
FIG. 7 is a control system block diagram of air filtration and purification system in accordance with some embodiments.

FIG. 7 is a control system block diagram of air filtration and purification system 22 in accordance with some embodiments of the present disclosure. The air filtration and purification system 22 contains control system 27 that includes a monitoring system 25 comprising a programmed logic circuit 24 and a plurality of sensors 23 positioned in critical areas of air filtration and purification generation system 22 for transmitting operating conditions to, and receiving commands from, the building control center (not shown here). Sensors 23 detect conditions at and around air filtration and purification generation system 22 and are operatively coupled to the program logic circuit 24. The sensors 23 deliver information to the programmed logic circuit 24 indicative of the operating state of air filtration and purification generation system 22. The operating state may include either nominal operating conditions or more critical conditions. For example, a sensor 23 might transmit signals to program logic circuit 24 indicating that the air conditioning system in HVAC Chamber 13C may require inspection for possible coolant problems. This information may be transmitted by sensor 23 as analog or digital signals utilizing parallel or serial transfer, and may be sent as data packets. The data may then be acted upon automatically by the program logic circuit 24 or manually by the system controller 26.

The program logic circuit 24 further includes a memory (not shown) storing a data structure associating received signal values with an operating condition value. The programmed logic circuit 24 includes a memory access circuit (not shown) operatively coupled to the memory configured to access the data structure and return the operating condition value associated with the operating state. The monitoring system 25 may transmit the operating condition data to system controller 26. Memory may be embedded in programmed logic circuit 24 in whole or in part, or may be a separate element operatively coupled to programmed logic circuit 24. Memory may include any forms of volatile random access memory (RAM') and some form or forms of non-volatile computer memory such as a hard disk drive, an optical disk drive, or an electrically erasable programmable read-only memory space (also known as 'EEPROM' or 'Flash' memory), or other forms of random access memory ('RAM').

The operation of the system may be altered during the different stages of use of the elevator. For instance, if the elevator is on standby and has not yet received a command (e.g., a passenger selecting a floor), the cabin air could be processed and circulated at a specified reduced level. When a passenger enters the cab, detection devices may record the event and command the processing equipment to immediately begin normal operations (i.e., processing and circulating air through the cab at a level above the reduced standby level. Following the selection of a floor, the cab is sent to that floor as specified by the new passenger. Should there be no other passengers in the cab, the elevator then continues to another location as required by the main elevator command center. Should the location be at a non-passenger location, the elevator can then return to standby and the air processing and circulation system would be returned to the reduced level.

Alternative embodiments may vary from the examples described above. For instance, in one embodiment, an alternate means to transfer filtered, purified air from the air processing array 13 located in the upper area of the hoistway 10 could eliminate the processed air conduit 14B and the exhaust air conduit 15. The processed air conduit 14B would be replaced with a light weight carbon fiber high pressure air vessel mounted on the top of the cab 2 and connected to the upper air chamber 17 of the cab 2 for the passenger consumption of processed air. Prior to the complete depletion of the processed air taken from the air vessel, the cab 2 would be commanded by the control system 27 to return to the air processing array 13 for the purpose of robotically exchanging the depleted air vessel with a stand-by, precharged vessel. The exchange of air vessels would be done rapidly during an optimum time increment as selected by the control system 27. The cab 2 exhaust air conduit 15 would be replaced by an exhaust fan to discharge the spent air from the cab 2 into the hoistway 10 where it would escape through the top of the building.

Another alternate means to transfer filtered, purified air from the air processing array 13 located in the upper area of the hoistway 10 would be to eliminate the processed air conduit 14B and the exhaust air conduit 15. The processed air conduit 14B would be replaced with a light weight carbon fiber high pressure air vessel mounted on the top of the cab 2 and connected to the upper air chamber 17 of the cab 2 for the passenger consumption of processed air. Prior to the complete depletion of the processed air taken from the high pressure air vessel, the cab 2 would be commanded under prescribed conditions by the control system 27 to stop at a floor where a fixed high pressure air service connection has been mounted to provide processed pressured air from a service conduit that is connected to the air processing array 13. Upon stopping, the cab 2, air vessel would be robotically coupled to the high pressure air service connection and the recharging of the air vessel would be done rapidly during an optimum time increment as selected by the control system 27. The air service conduit would connect to the air processing array 13 and extend the vertical span of the building to service all floors with a high pressure air service connection at each floor. The cab 2 exhaust air conduit 15 would be replaced by an exhaust fan to discharge the spent air from the cab 2 into the hoistway 10 where it would escape through the top of the building.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, product, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, a term preceded by "a" or "an" (and "the" when antecedent basis is "a" or "an") includes both singular and plural of such term, unless clearly indicated within the claim otherwise (i.e., that the reference "a" or "an" clearly indicates only the singular or only the plural). Also, as used in the description herein and throughout the meaning of "in" includes "in" and "on" unless the context clearly dictates otherwise.

Reference throughout this specification to "one embodiment", "an embodiment", or "a specific embodiment" or similar terminology means that a particular feature, structure, or characteristic described in connection with the embodiment is included in at least one embodiment and may not necessarily be present in all embodiments. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

Additionally, any examples or illustrations given herein are not to be regarded in any way as restrictions on, limits to, or express definitions of, any term or terms with which they are utilized. Instead, these examples or illustrations are to be regarded as being described with respect to one particular embodiment and as illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," "in one embodiment."

Thus, while the invention has been described with respect to specific embodiments thereof, these embodiments are merely illustrative, and not restrictive of the invention. Rather, the description is intended to describe illustrative embodiments, features and functions in order to provide a person of ordinary skill in the art context to understand the invention without limiting the invention to any particularly described embodiment, feature or function, including any such embodiment feature or function described. While specific embodiments of, and examples for, the invention are described herein for illustrative purposes only, various equivalent modifications are possible within the spirit and scope of the invention, as those skilled in the relevant art will recognize and appreciate.

As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component.

What is claimed is:

1. A system for processing air for a passenger elevator, the system comprising:
    a stationary exterior air inlet positioned to receive exterior air;
    a first air conduit which is separate from a hoistway of a building through which the elevator cab travels, the first conduit having a first end coupled to the stationary exterior air inlet and a second end configured to be coupled to an elevator cab, wherein the first air conduit is configured to deliver the exterior air to the elevator cab;
    a stationary air handler coupled to the first air conduit, wherein the stationary air handler is configured to pressurize the exterior air and cause the exterior air to flow into the elevator cab; and
    a second air conduit which is separate from the first air conduit and the hoistway, the second air conduit having a first end configured to be coupled to the elevator cab and a second end configured coupled to a stationary exhaust exit port, wherein the second air conduit is configured to exhaust air from the elevator cab to the stationary exhaust exit port;
    wherein the first air conduit and the second air conduit are flexible traveling conduits that are configured to maintain the respective couplings to the elevator cab and continue to deliver the exterior air from the stationary exterior air inlet to the elevator cab and exhaust air from the elevator cab to the stationary exhaust exit port while the elevator cab travels through the hoistway.

2. The system of claim 1, wherein the first air conduit is separate from a building heating, ventilation and cooling system, the first air conduit comprising an exterior air conduit located in an uppermost area of the building, the exterior air conduit being coupled between the exterior air inlet and the air handler, the first air conduit further comprising a processed air conduit that is coupled between the air handler and the elevator cab.

3. The system of claim 2, wherein the air handler includes an air filter, and an air purifier, and at least one of a heater and a cooler, the air handler being configured to provide pressurized, processed air to a pressure plenum, and wherein the pressurized, processed air in the pressure plenum is delivered to the processed air conduit.

4. The system of claim 3, wherein the air purifier comprises one or more ultraviolet air purifier units located in the uppermost area of the building which regulate the purity of ambient supply air as required by the control system to meet pre-set requirements.

5. The system of claim 2, wherein the traveling conduits comprise lightweight corrugated plastic conduits.

6. A system for processing air for a passenger elevator, the system comprising:
an exterior air inlet positioned to receive exterior air;
a first air conduit having a first end coupled to the exterior air inlet and a second end configured to be coupled to an elevator cab, wherein the first air conduit is configured to deliver the exterior air to the elevator cab;
an air handler coupled to the first air conduit, wherein the air handler is configured to pressurize the exterior air and cause the exterior air to flow into the elevator cab; and
a second air conduit having a first end configured to be coupled to the elevator cab and a second end configured coupled to an exhaust exit port, wherein the second air conduit is configured to exhaust air from the elevator cab to the exhaust exit port;
wherein the first air conduit and the second air conduit are traveling conduits that are configured to maintain the respective couplings to the elevator cab and continue to deliver the exterior air to the elevator cab and exhaust air from the elevator cab to the exhaust exit port while the elevator cab travels through a hoistway of a building;
the system further comprising one or more emergency valves coupled to the first and second air conduits, wherein the system is configured to operate alternately in either a normal operational mode or an emergency mode, wherein in the normal operational mode, the one or more emergency valves are positioned to enable the flow of exterior air through the first air conduit, the elevator cab and the second air conduit, and wherein in the emergency mode, the one or more emergency valves are positioned to block the flow of exterior air into the elevator cab from the first air conduit and to block the exhaust of air from the elevator cab out through the second air conduit.

7. The system of claim 6, further comprising an emergency air source, wherein in the emergency mode, the emergency air source is coupled to the first air conduit and provides air to the elevator cab through the first air conduit.

8. The system of claim 1, further comprising a control system which is coupled to the air handler and includes one or more sensors and a monitor which are jointly operable to record and control the quality, rate, temperature and pressure of air being processed by the air handler.

9. The system of claim 8, wherein the air handler includes an air filter and an air purifier, wherein the control system includes a system controller which is operable in an automatic mode in which the system controller automatically adjusts the air filter and purifier to predetermined levels and is operable in a manual mode in which manual and remote operation of the air filter and purifier is enabled.

10. The system of claim 8, wherein the control system monitors and controls an exterior air conduit located in an uppermost area of the building and thereby regulates a supply rate of exterior air.

11. The system of claim 8, wherein the control system is configured to monitor of one or more air filter systems coupled with air blowers that are located in an uppermost area of the building and thereby regulates a supply rate of exterior air.

12. The system of claim 8, wherein the control system is configured to monitor and control one or more heating, ventilation, air conditioning (HVAC) units and thereby regulate the temperature of the air supplied to the elevator cab.

13. The system of claim 8, wherein the control system is configured to monitor and control the pressure plenum and thereby regulate the pressure of the air supplied to the elevator cab.

14. The system of claim 8, wherein the control system is configured to monitor and control an air supply rate in the first air conduit to meet predetermined flow rate requirements.

15. The system of claim 8, wherein the control system is configured to monitor and control an air exhaust rate in the second air conduit to meet predetermined flow rate requirements.

16. The system of claim 1, wherein at least one of the first air conduit and the second air conduit is secured to a traveling electrical cable.

17. The system of claim 16, wherein each of both the first air conduit and the second air conduit has a length of the traveling electrical cable and is ace secured to the traveling electrical cable.

18. The system of claim 1, wherein each of the first air conduit and the second air conduit and the traveling electrical cable hangs below the elevator cab.

19. The system of claim 1, wherein the exterior air to the elevator cab maintains air pressure in the elevator cab at a level greater than an ambient air pressure external to the elevator cab, thereby preventing air in the hoistway from passing into the elevator cab.

20. The system of claim 1, wherein the elevator cab is configured to move vertically within the hoistway.

* * * * *